United States Patent [19]

Van Assche et al.

[11] Patent Number: 4,472,194
[45] Date of Patent: Sep. 18, 1984

[54] INCREASING YIELDS OF VEGETABLE CROPS WITH O-PHENYL HYDROXYLAMINES

[75] Inventors: Charles J. Van Assche, Marseilles; Jean-Jacques Herve, Aubagne; Pierre M. Carles, Marseilles, all of France

[73] Assignee: Roussel UCLAF, Paris, France

[21] Appl. No.: 462,084

[22] Filed: Jan. 28, 1983

[30] Foreign Application Priority Data

Jan. 28, 1982 [FR] France ............... 82 01321

[51] Int. Cl.³ ............................................. A01N 33/10
[52] U.S. Cl. .......................................... 71/121; 71/77
[58] Field of Search ................................. 71/121, 77

[56] References Cited

U.S. PATENT DOCUMENTS 3,686,237 8/1972 Hirsch ............................... 260/397.3

OTHER PUBLICATIONS

Aksanoua et al., Chem. Abst., vol. 82, (1975) 139982h.
Hirch, Chem. Abst., vol. 83, (1975) 43608k.
Endo et al., Chem. Abst., vol. 93, (1980) 149948t.
Bauer et al., Chem. Abst., vol. 68, (1968) 21678w.

Primary Examiner—Catherine L. Mills
Attorney, Agent, or Firm—Charles A. Muserlian

[57] ABSTRACT

Novel compositions for increasing the growth of vegetables comprising a growth increasing amount of at least one compound selected from the group consisting of a compound of the formula

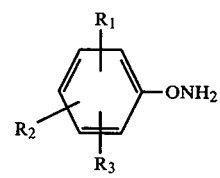

wherein either $R_1$ is hydrogen, $R_2$ is hydrogen and $R_3$ is selected from the group consisting of hydrogen, nitro in the 2- or 4-position, methyl in the 2-, 3- or 4-position, chlorine in the 3- or 4-position and bromine or $-CF_3$ in the 4-position or $R_2$ is nitro in the 2 position and $R_3$ is nitro or $-CF_3$ in the 4 position or $R_1$ is 2-$NO_2$, $R_2$ is 4-$NO_2$ and $R_3$ is 6-$NO_2$ or $R_2$ is 6-$NO_2$ and $R_3$ is 4-$CF_3$ and their non-toxic, acid addition salts and an agricultural carrier and a method of increasing the growth of vegetables.

10 Claims, 3 Drawing Figures

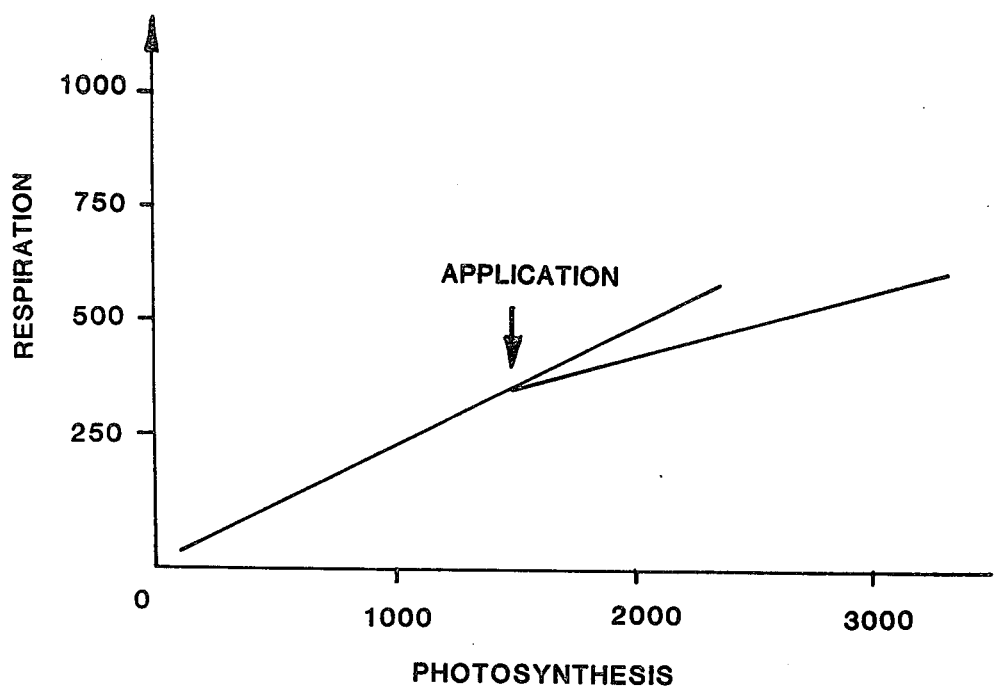

INCREASING YIELDS OF VEGETABLE CROPS WITH O-PHENYL HYDROXYLAMINES

STATE OF THE ART

The compounds of formula I are known in the literature such as Chem. Abs., Vol. 82 (21), No. 139982h, Chem. Abs., Vol. 83(5), No. 43608, Chem. Abs., Vol. 88(9), No. 65075d, Chem. Abs., Vol. 93(15), No. 149948t and Chem. Abs., Vol. 68(5), No. 21678w as well as German Pat. No. 2,059,190. However, their use in the agricultural field is not known.

OBJECTS OF THE INVENTION

It is an object of the invention to provide novel compositions for increasing the growth of vegetables.

It is another object of the invention to provide a novel method of increasing the growth of vegetables.

These and other objects and advantages of the invention will become obvious from the following detailed description.

THE INVENTION

The novel compositions of the invention for increasing the growth of vegetables are comprised of a growth increasing amount of at least one compound selected from the group consisting of a compound of the formula

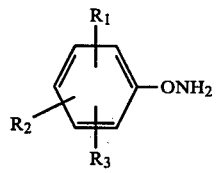

wherein $R_1$ is hydrogen, $R_2$ is hydrogen and $R_3$ is selected from the group consisting of hydrogen, nitro in the 2- or 4-position, methyl in the 2-, 3- or 4-position, chlorine in the 3- or 4-position and bromine or —$CF_3$ in the 4-position or $R_2$ is nitro in the 2 position and $R_3$ is nitro or $CF_3$ in the 4-position or $R_1$ is 2-$NO_2$, $R_2$ is 4-$NO_2$ and $R_3$ is 6-$NO_2$ or $R_2$ is 6-$NO_2$ and $R_3$ is 4-$CF_3$ and their non-toxic, acid addition salts.

Examples of suitable acids for the acid addition salts are inorganic acids such as hydrochloric acid, hydrobromic acid, sulfuric acid or nitric acid and organic acids such as trifluoroacetic acid.

Among the preferred compounds of formula I are 0-(4-nitrophenyl)-hydroxylamine,0-(4-phenyl)-hydroxylamine and 0-(4-chlorophenyl)-hydroxylamine and their acid addition salts, especially their hydrochlorides. Also preferred are 0-(2-nitrophenyl)-hydroxylamine, 0-(2,4-dinitrophenyl)-hydroxylamine, 0-(2-nitro-4-trifluoromethylphenyl)-hydroxylamine, 0-(4-methylphenyl)-hydroxylamine, 0-(4-bromo-phenyl)-hydroxylamine and 0-(2-nitro-4-chloro-phenyl)-hydroxylamine and their acid addition salts.

The compounds of formula I may be made by known processes such as reacting a compound of the formula

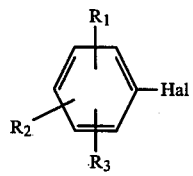

wherein $R_1$, $R_2$ and $R_3$ have the above definitions and Hal is a halogen with hydroxylamine to obtain the corresponding compound of formula I or reacting a compound of the formula

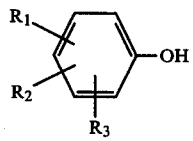

wherein $R_1$, $R_2$ and $R_3$ have the above definitions with $NH_2$—O—$SO_3H$ to obtain the corresponding compound of formula I which optionally can be reacted with an approximately stoichiometric amount of an acid to form the acid addition salt.

The compositions of the invention are useful in agriculture to improve the physiological state of cultivated vegetables and to obtain increased harvest weight. The experimental data infra shows on diverse parts of the plant an action lessening the inhibition of oxygen in photosynthesis. This phenomen is constant in all the tests effected. The described tests studied the activity of the compounds of formula I and their acid addition salts by the "Warburg effect", the activity of 0-(4-nitrophenyl)-hydroxylamine on oxygen toxicity vis-a-vis photosynthesis of protoplasts of wheat leaves, the activity of 0-(4-nitrophenyl)-hydroxylamine on oxygen toxicity vis-a-vis photosynthesis of intact chloroplasts extracted from wheat leaves and the effect of 0-(4-nitrophenyl)-hydroxylamine on the carbon balance of plants.

Other tests shown the weight increase of the treated plants, especially on tomatoes and soybeans when treated with 0-(4-nitrophenyl)-hydroxylamine. The tests show the compositions to be effective on diverse crops with respect to the nature of the harvested organs such as roots, pods, seeds, fruits and leaves. The tests show that the compositions are useful on various plants such as soybeans, wheat, barley, oats, cotton, beans, rosaceae and composaceae and specifically on so-called plants "in $C_3$" or the plants whose first product formed in the course of photosynthesis is a molecule of 3 carbon atoms.

The compositions of the invention have the effect of diminishing the inhibition of photosynthesis by oxygen. The same nature of the mode of action by lessening the inhibiting effect of oxygen on photosynthesis considering the perspectives to occur all the more remarkable and surprising for increasing the crop yield of plants so-called "in $C_3$". This mode of action equally acts as a consequence to increase in a substantial manner the quantity of oxygen rejected in the atmosphere by the treated plants which offers a non-negligible ecological aspect before the actual problems of increasing carbon dioxide in the atmosphere.

The preferred compositions of the invention for increasing the yields of vegetables contain as the active ingredient 0-(4-nitrophenyl)-hydroxylamine, 0-phenylhydroxylamine or 0-(4-chlorophenyl)-hydroxylamine and their acid addition salts, especially their hydrochlorides.

The compositions may be in the form of powders, granules, suspensions, emulsions or solutions containing the active ingredient. Examples of suitable agricultural carriers are aqueous or non-aqueous vehicles preferably containing a non-ionic, cationic or anionic surface active agent to ensure a uniform dispersion of the components of the composition. The vehicle may be a liquid such as water, alcohol, hydrocarbons or other organic solvents, a mineral, animal or vegetable oil or a powder such as talc, clays, silicates and kieselguhr.

The solid compositions in the form of powders for powdering, wettable powders or granules may be prepared by mixing the active compound with an inert solid or by impregnating a solid support with a solution of the active ingredient and evaporating the solvent.

The compositions may contain besides the vehicle and the surface active agent and the active compound one or more other substances for influencing the increase of plants. The compositions normally will contain 10 to 80% by weight, preferably 10 to 50% by weight of the compounds of formula I or their acid salts.

The novel method of increasing the growth of plants comprises applying to the plant crop a sufficient amount of at least one compound of formula I and their acid salts to increase the growth of the plants. The dose of active compound will vary depending upon the vegetable treated, the nature of the soil, atmospheric conditions and the stage of growth of the vegetable and the specific compound selected. The usual useful dose is 20 to 500 g/ha, preferably 40 to 120 g/ha.

FIG. 3 is a graph similar to FIG. 2 showing the reuslts of application of the active substance to the roots of sugar beets.

Figure 1:
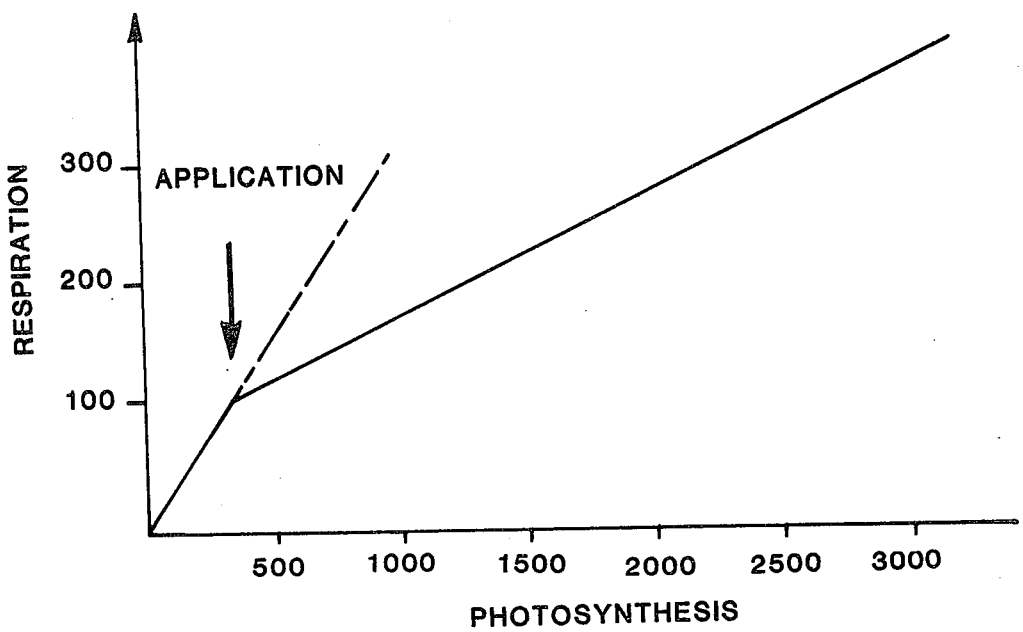
FIG. 1 is a graph of respiration against photosynthesis before and after treatment of leaves of wheat plants.

In the following examples there are described several preferred embodiments to illustrate the invention. However, it is to be understood that the invention is not intended to be limited to the specific embodiments.

EXAMPLE 1

An emulsifiable concentrate was prepared containing by weight 15% of 0-(4-nitrophenyl)-hydroxylamine, 6.4% of Atlox 4851 (oxyethylene triglyceride with a sulfonate having an acid index of 1.5), 3.2% of Atlox 4855 (oxyethylene triglyceride with a sulfonate having an acid index of 3) and 75.4% of xylene.

EXAMPLE 2

A wettable powder was prepared containing by weight 25% of 0-(4-nitrophenyl)-hydroxylamine, 15% of Ekapersol (condensation product of sodium naphthalenesulfonate), 35% of Zeosil 39 (hydrated synthetic silica obtained by precipitation and 25% of Vercoryl S (colloidal kaolin). Another wettable powder was prepared containing 25% of 0-(4-chlorophenyl)-hydroxylamine, 15% of Ekapersol, 35% of Zeosil 39 and 25% of Vercoryl S.

EXAMPLE 3

An emulsifiable concentrate was prepared containing by weight 15% of 0-phenyl-hydroxylamine hydrochloride, 6.4% of Atlox 4851, 3.2% of Atlox 4855 and 75.4% of xylene.

TEST DATA

A. Study of "Warburg effect"

The products of formula I are capable of diminishing the inhibiting effect of oxygen on photosynthesis (Warburg effect) which as a consequence stimulates photosynthesis and increases crop yields. The test was effected on cut wheat leaves floating or in distilled water or a solution of 10 mmoles/liter of the test compound. The leaves were placed in glass tight chambers with a lighting of 300 W/m$^2$ and the temperature was regulated at 25° C. The atmosphere in the chamber was constantly renewed either with normal air (21% oxygen—350 ppm of $CO_2$) or with 100% pure oxygen. When constant photosynthesis was attained, 0.09$\mu$ moles of $^{14}CO_2$ (specific activity—22 mCi/mM) were introduced and the leaves were left for 15 minutes in light in the presence of radioactive carbon dioxide. The leaves were then plunged into liquid nitrogen and were stored. Then, the leaves were burned to determine the amount of $^{14}CO_2$ fixed by photosynthesis and the results were compared with respect to the radioactivity for the controls and the treated leaves.

When the leaves were treated with 10$\mu$ moles of the test product and placed in a 100% oxygen atmosphere, the photosynthesis was stimulated 15 to 50%, i.e. 18% with 0-(4-chloro-phenyl)-hydroxylamine hydrochloride with respect to the controls. In the controls, oxygen inhibited photosynthesis by 15 to 45%. The said results show that the compounds of formula I strongly raised the inhibition of oxygen to photosynthesis (Warburg effect).

B. Activity of 0-(4-nitro-phenyl)-hydroxylamine to oxygen toxicity to photosynthesis of wheat leaf protoplasts The protoplasts of wheat leaves were extracted by known techniques for isolation by maceration of vegetable material in cellulosolytic and pectinolytic enzymatic solutions as well as by differential centrifugation and filtration. The inhibiting effect of oxygen was measured on protoplast suspension as a function of treatment with 0-(4-nitro-phenyl)-hydroxylamine.

The test consisted of causing variation of the ratio of oxygen and $HCO_3^\ominus$ concentrations in the protoplast suspensions in the presence and absence of the test compound. The photosynthesis was evaluated by measuring the oxygen released by photosynthesis in light and effected with a Clark type electrode at a temperature of 25° C. The lighting in the measured cell corresponded to 250 W/m$^2$. The values of the level of photosynthesis observed as a ratio of $HCO_3^\ominus$ to $O_2$ in the presence or absence of 40 $\mu$M of the test compound is reported in Table I.

TABLE I

| Ratio of $(CO_3H^-)$ / $(O_2)$ | Photosynthesis of controls in $\mu$ moles of $O_2$ released mg of chlorophyll hour | Photosynthesis obtained in presence of 40 $\mu$M of 0-(4-nitrophenyl)-hydroxylamine | |
|---|---|---|---|
| | | in $\mu$moles of $O_2$ released/mg of chlorophyll/hour | in % with respect to controls |
| 2.25 × 10$^{-3}$ | 196 | 198 | 101 |
| 1.10 × 10$^{-3}$ | 108 | 122 | 112 |
| 6.7 × 10$^{-4}$ | 76 | 96 | 126 |
| 3.3 × 10$^{-4}$ | 36 | 68 | 188 |
| 1.1 × 10$^{-4}$ | 26 | 58 | 223 |

The results of Table I show that 0-(4-nitro-phenyl)-hydroxylamine strongly diminishes oxygen toxicity to photosynthesis as shown by the increase in the level of photosynthesis of treated wheat protoplasts, especially when the relative concentrations of bicarbonate and oxygen are such that photosynthesis is inhibited (Warburg effect).

C. 0-(4-nitrophenyl)-hydroxylamine activity against oxygen activity on photosynthesis by intact chloroplasts extracted from wheat leaves Intact chloroplasts designated as Class A by the terminology of Hall [Nature, Vol. 235 (1978), p. 125-126] are capable of fixing carbon dioxide and releasing oxygen at a level equivalent to that of a whole leaf (50 to 250$\mu$ moles of oxygen released per mg of chlorophyl per hour). The chloroplasts used in the test were extracted from wheat leaf protoplasts and were obtained by mild mechanical rupturing of cell walls by osmotic shock, filtration and centrifugation by gradients of density. The photosynthesis was evaluated by measuring the oxygen released by a suspension of intact chloroplasts in light in the presence of $HCO_3^\ominus$ and oxygen in varying relative proportions in the presence or absence of 40 $\mu$M of 0-(4-nitrophenyl)-hydroxylamine and the results are reported in Table II.

TABLE II

| Ratio of $\frac{(CO_3H)^-}{(O_2)}$ | Photosynthesis of controls in $\mu$ moles of $O_2$ released/mg of chlorophyll/hour | Photosynthesis obtained in presence of 40 $\mu$M of 0-(4-nitrophenyl)-hydroxylamine | |
|---|---|---|---|
| | | In $\mu$ moles of $O_2$ released/mg of chlorophyll/hour | In % of controls |
| $10^{-3}$ | 114 | 120 | 105.2 |
| $4 \times 10^{-3}$ | 76 | 100 | 131.5 |
| $3.2 \times 10^{-3}$ | 36 | 70 | 194.4 |
| $1.1 \times 10^{-4}$ | 26 | 56 | 215.4 |

The stimulation of intact chloroplast photosynthesis with 0-(4-nitro-phenyl)-hydroxylamine, especially when the ratio of concentrations of $HCO_3^\ominus$ and oxygen diminish, is shown clearly by the product suppressing the toxic effect of oxygen on photosynthesis resulting in an increase in that of treated chloroplasts as compared to the controls.

D. Effect of 0-(4-nitro-phenyl)-hydroxylamine on carbon balance of plants 0-(4-nitro-phenyl)-hydroxylamine stimulates the photosynthesis of treated chloroplasts, protoplasts and leaves as compared to controls by increasing oxygen inhibition of photosynthesis. This property originally resulted in a stimulation of photosynthesis of the entire plant when it was treated either by root application or foliar application of the product. The experimental arrangement permitting the measurement of photosynthesis was based on a compensation method of starting from a value on the order of 350 ppm of carbon dioxide which corresponds to a modification of the experimental procedure of Andre et al [Ann. Agron., Vol. 30 (1979), No. 2, p. 139-151]. The plants were enclosed in a glass chamber with an interior volume of 6.250 liters continuously swept at a velocity of 0.5 m/sec$^{-1}$ with 70% humid air. The plants were lit by 5 OSRAM (HQI) lamps of 250 W each for hemeroperiods of 12 hours. The drawing out of carbon dioxide from the air provided to the assimilation chambers was analyzed by an infra-red URAS 2-T (Hartman and Braun) analyzer. The concentration in carbon dioxide was restored to 350 ppm by injecton of the gas coming from a compressed carbon dioxide cylinder and regulation was assured by Eurotherm (type 070) regulators. The number of carbon dioxide injections were counted and registered with computers and Sodeco imprinters. The microcliamatological parameters were registered with Shessel registers.

During the night, the system was deactivated and only the variations of carbon dioxide content were directly registered after determination by infra-red analysis. The values of carbon dioxide supplied in the light measured by the number of gas injections per time unit gave a raw measure of photosynthesis. The rejection of carbon dioxide by the plant in darkness furnished an estimation of respiration. It was interesting to measure the effects of 0-(4-nitrophenyl)-hydroxylamine on the carbon balance of treated plants by studying the evolution of the relative values of photosynthesis and respiration. The method proved to be an adaptation of the test of McCree et al. [Crop Science, Vol. 18 (1978), p. 13-18].

To avoid the problem of heterogeneity existing between the plants and the inevitable variation in characteristics of the assimilation chambers used, each plant or group of plants were not treated with 0-(4-nitrophenyl)-hydroxylamine until 7 days after the beginning of the measurements and this period acted as a control. On the 7th day, the plants were treated either on the leaves or at their roots with the test compound and the photosynthesis and respiration effected were measured continuously for 7 days which corresponded to a treatment.

For the foliar application, the wettable powder described above containing 25% by weight of 0-(4-nitrophenyl)-hydroxylamine was sprayed onto the plants so that the final concentration of active material was $10^{-5}$ M. After drying of the suspension, the plants were replaced in the assimilation chambers and the photosynthesis and respiration were measured. The results were graphed with the abscissa being the photosynthesis values obtained during the hemeroperiod and ordinates being the respiration values measured during the nyctoperiod succeeding the hemeroperiod. In 2 cases, the values are expressed in time of opening of electrovanes permitting to attain the value assigned to 350 ppm of carbon dioxide (photosynthesis) or the time of opening of electrovanes leading to air going out of the chambers to a carbon dioxide trap to restore the carbon dioxide level to 350 ppm (respiration). The graph of FIG. 1 shows the evolution of the ratio of photosynthesis and respiration after foliar treatment to wheat leaves (Triticum sativum-variety Capitole).

From FIG. 1 when the straight line drawn through the experimental points obtained deviates from that representing the untreated controls, the angle formed indicates the fullness of the influence of the treatment either towards a favorable carbon balance (photosynthesis proportionally more stimulated then respiration - the straight line is inclined to the abscissa axis) or towards an unfavorable balance (respiration proportionately more stimulated than photosynthesis-straight line inclined towards ordinate axis). The example of FIG. 1 shows that the carbon balance of wheat treated with 0-(4-nitro-phenyl)-hydroxylamine was favorable since photosynthesis was strongly stimulat with respect to respiration and provided an increase in the level of photosynthesis caused by the compound and provided a rise of inhibition of photosynthesis by oxygen as shown by tests A,B and C. In the test with wheat, the photosynthesis stimulation was 30 to 60%.

Figure 2:
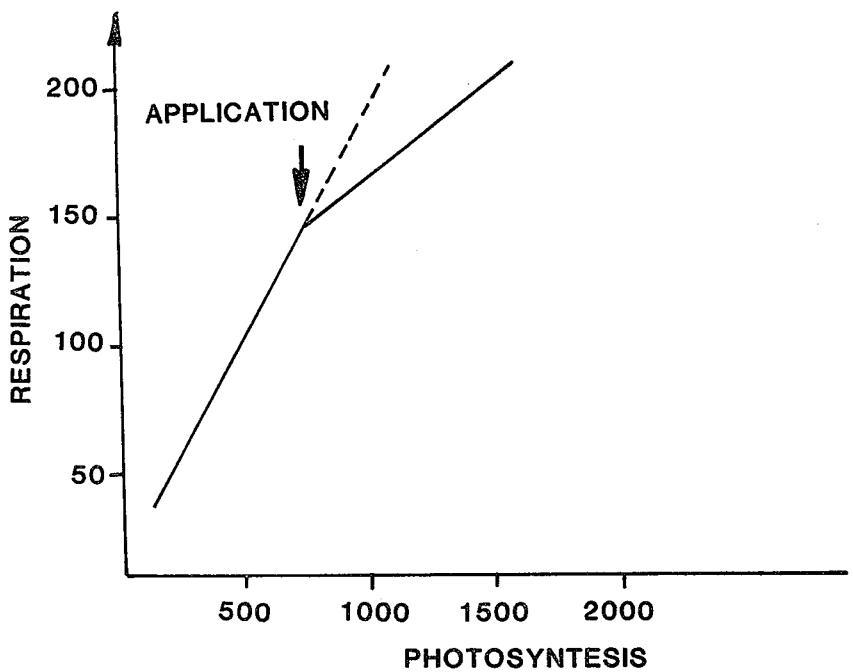
FIG. 2 is a graph similar to that of FIG. 1 except that the active substance was applied to the roots of the wheat plant.

For root application, the plants were grown in a nutritive solution of Arnon and Hoagland and 0-(4-nitro-phenyl)-hydroxylamine was applied in the form of a 25% by weight of a wettable powder diluted directly with the nutritive solution. The gaseous exchange was measured using the same experimental apparatus discussed above and the results were graphed by the modified method of McCree et al. In the case of wheat, (*Triticum sativum* - Capitol variety), the active compound was applied at a final concentration of $10^{-5}$ M and the results are reported in FIG. 2.

The inclination of the straight line towards the abscissa axis after treatment with 0-(4-nitro-phenyl)-hydroxylamine clearly shows that photosynthesis was strongly stimulated as compared to respiration and it can be observed as a general rule, a stimulation on the order of 28 to 55% for wheat.

The said test was repeated with sugar beets (*Beta vulgaris*-Ceres Monogerm variety) and FIG. 3 shows the results obtained with the said root application. The direction of the line after application of 0-(4-nitro-phenyl)-hydroxylamine at a final concentration of $10^{-5}$ M in the form of a 25% wettable powder demonstrates the favorable effect on photosynthesis as compared to respiration. The stimulation observed on sugar beets generally was on the order of 30 to 40%.

As a conclusion, the different laboratory studies reported above realized on organites, isolated organs or the entire plant show that 0-(4-nitro-phenyl)-hydroxylamine on the plants studied eliminated oxygen toxicity to photosynthesis. One of the important consequences of this discovery is the inhibition level (Warburg effect) obtained which as a consequence is a very important increase of photosynthesis of plants treated with the said compound. This original property of the said compound leads to an increase in yields of cultivated crops treated therewith as can be seen from the following tests.

E. Tests on tomatoes

This test was effected on a crop of tomatoes of Europcel variety using a Fisher block in 5 repeats. The elementary parcels were 20 m² (10 m×2 m) and an untreated control was included in each repeat. The crop was planted in a calcaro-muddy, clay-like soil and treatments were effected with a Van der Weij apparatus with a base of 750 l/ha at constant pressure of 3 bars. The treatments were effected either after the falling of the petals of the first flowers ($T_1$) or after the falling of the petals of the last flowers $T_2=(T_1+20$ days) or at the moment of formation of the fruits $T_3=(T_2+20$ days). 0-(4-nitro-phenyl)-hydroxylamine was applied at doses of 40, 60 or 120 g/ha 3 times or once. Two tomato crops were made and the yield for each crop was determined in kg for 32 tomato plants and was compared to the yield of untreated plants and the results are reported in Table III.

TABLE III

| Doses in g/ha | | | Yield in % as compared to controls | | |
|---|---|---|---|---|---|
| $T_1$ | $T_2$ | $T_3$ | First crop $J_1$ | Second crop $J_1 + 12$ | Total |
| | 60 g | | 101.3 | 108.5 | 104.4 |
| | 120 g | | 100.9 | 138.3 | 111.9 |
| 120 g | | | 115.2 | 104.1 | 112.6 |
| | | 120 g | 111.4 | 105.9 | 111.2 |
| 40 g | 40 g | 40 g | 100.6 | 121.4 | 107.2 |
| Con-trols | | | 100→ 25.4 kg | 100→ 8.9 kg | 100→ 34.3 kg |

Table III clearly shows that 0-(4-nitro-phenyl)-hydroxylamine possesses an activity to increase the yield of tomatoes.

F. Test on soybeans

This test was effected on a crop of soybeans using a Fisher block in 6 repeats with elementary parcels of 40 m² (15 m×2.66 m) using an untreated control in each repeat. The crops were planted in a sandy calcaro-clay-like soil and the treatments were based on 1000 l/ha with a constant pressure of 3 bars with a Van der Weij apparatus. The stages of treatment were at $T_1$ (appearance of flower buttons), $T_2$ (formation of first silics) and $T_3$ (end of formation of silics) and 0-(4-nitro-phenyl)-hydroxylamine was applied at doses of 40, 60 or 120 g/ha once, twice or three times. The yield was determined in kg for 5 soybean plants and the results are reported in Table IV with the controls being 100%.

TABLE IV

| Doses in g/ha | | | |
|---|---|---|---|
| $T_1$ | $T_2$ | $T_3$ | % Yield |
| 120 | | | 107.8 |
| | 120 | | 110.5 |
| | | 120 | 117.6 |
| 60 | | | 105.7 |
| | 60 | | 105.2 |
| | | 60 | 102.4 |
| 40 | 40 | 40 | 104.6 |
| 60 | 60 | | 102.8 |
| | 60 | 60 | 116.0 |
| 60 | | 60 | 107.0 |
| Control | | | 100 |

The results of Table IV show that 0-(4-nitro-phenyl)-hydroxylamine possesses the ability to increase the yield of soybeans.

In another series of tests on soybeans under subtropical conditions such as in Brazil, a very improtant increase in yield of grains was obtained with 0-(4-nitro-phenyl)-hydroxylamine. The test was effected on IAC-6 variety of soybeans with a Fisher block of 4 repeats with elementary parcels of 30 m² and untreated control in each repeat. The applications were made once, twice or 4 times and the stages of treatment were $T_1$ (flowering beginning -60 days after seeding), $T_2$ (74 days after seeding), $T_3$ (86 days after seeding— beginning of filling in of grain) and $T_4$ (96 days after seeding) and 0-(4-nitro-phenyl)-hydroxylamine was applied at doses of 60, 120 and 240 g/ha in the form of a 25% by weight wettable powder. The results were expressed in kg of grains per ha with the controls being 100% and the results are reported in Table V.

TABLE V

| Doses in g/ha | | | | |
|---|---|---|---|---|
| $T_1$ | $T_2$ | $T_3$ | $T_4$ | % Yield |
| | 120 | 120 | | 113.6 |
| 120 | 120 | 120 | 120 | 126 |
| 60 | 60 | 60 | 60 | 126.7 |
| Control | | | | 100 |

The results of Table V show that 0-(4-nitro-phenyl)-hydroxylamine increases the yield of soybean crops.

In another test with BR-1 soybean variety under different climatic conditions (very high degree of rain and very high temperatures), 0-(4-nitro-phenyl)-hydroxylamine was applied with an identical procedure at $T_1$ (55 days after planting-beginning of flowering), $T_2$ (70 days after planting-pod development), $T_3$ (80 days after planting-grain development) and $T_4$ (90 days after planting-beginning senesence). The results expressed in yields of grains per ha are reported in Table VI.

TABLE VI

| Doses in g/ha | | | | |
|---|---|---|---|---|
| $T_1$ | $T_2$ | $T_3$ | $T_4$ | % Yield |
|  |  | 240 |  | 163 |
| 120 |  | 120 |  | 161 |
|  |  | 120 |  | 151 |
| 60 | 60 | 60 | 60 | 131 |
| 120 | 120 | 120 | 120 | 175 |
|  | Control |  |  | 100 |

Table VI shows that 0-(4-nitro-phenyl)-hydroxylamine increases the yield of soybean grains.

G. Tests on wheat 0-(4-nitro-phenyl)-hydroxylamine in the form of a 25% by weight wettable powder was sprayed onto winter wheat (*Triticum sativum* - Lutin variety) and the treatments were effected $T_0$ (second nodes formed), $T_1$ (first swelling - sheath of the last leaf emerged), $T_2$ (70% or earing), $T_3$ (flowering), $T_4$ (flowering), $T_5$ (milky grain) and $T_5$ (floury grain). The harvested grains were weighed and the yields expressed as quintals per hectare are reported in Table VII.

TABLE VII

| Doses in g/ha | | | | | | | Yield | |
|---|---|---|---|---|---|---|---|---|
| $T_0$ | $T_1$ | $T_2$ | $T_3$ | $T_4$ | $T_5$ | $T_6$ | kg/ha | % Yield |
|  | 500 |  |  |  |  |  | 64.25 | 104.05 |
|  |  | 250 |  |  |  |  | 66.00 | 106.88 |
| 62.5 | 62.5 | 62.5 | 62.5 | 62.5 | 62.5 | 62.5 | 64.62 | 104.66 |
|  | 125 | 125 | 125 | 125 | 125 | 125 | 64.62 | 104.66 |
|  | Control |  |  |  |  |  | 61.17 | 100 |

The results of Table VII show that 0-(4-nitro-phenyl)-hydroxylamine increases the yield of winter wheat.

Various modifications of the products and methods of the invention may be made without departing from the spirit or scope thereof and it is to be understood that the invention is intended to be limited only as defined in the appended claims.

What we claim is:

1. A method of increasing the yields of vegetable crops comprising applying to vegetable crops a growth increasing amount of at least one compound selected from the group of a compound of the formula

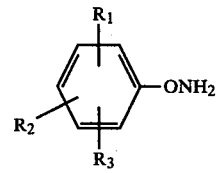

wherein either $R_1$ is hydrogen $R_2$ is hydrogen and $R_3$ is selected from the group consisting of hydrogen, nitro in the 2- or 4-positions, methyl in the 2-, 3- or 4-position, chlorine in the 3- or 4-position and bromine or $-CF_3$ in the 4-position or $R_2$ is nitro in the 2- position and $R_3$ is nitro or $-CF_3$ in the 4 position or $R_1$ is 2-$NO_2$, $R_2$ is 4-$NO_2$ and $R_3$ is 6-$NO_2$ or $R_2$ is 6-$NO_2$ and $R_3$ is 4-$CF_3$ and their non-toxic, acid addition salts.

2. The method of claim 1 wherein the active compound is applied at a rate of 20 to 500 g per hectare.

3. The method of claim 1 wherein the active compound is selected from the group consisting of 0-phenyl-hydroxylamine and its non-toxic, acid addition salts.

4. the method of claim 1 wherein the active compound is selected from the group consisting of 0-(4-chloro-phenyl)-hydroxylamine and its non-toxic, acid addition salts.

5. The method of claim 1 wherein the active compound is selected from the group consisting of 0-(4-nitro-phenyl)-hydroxylamine.

6. The method of claim 1 wherein the active compound is in the form of its hydrochloride salt.

7. The method of claim 1 wherein the vegetable crop is selected from the group consisting of soybeans, wheat, barley, oats, cotton, tomatoes, beans, rosaceae and composaceae.

8. The method of claim 1 wherein the crop is wheat.

9. The method of claim 1 wherein the crop is soybean.

10. The method of claim 1 wherein the crop is sugar beets.

* * * * *